United States Patent
Otto et al.

(10) Patent No.: US 7,824,333 B2
(45) Date of Patent: Nov. 2, 2010

(54) DIABETES MANAGEMENT METHODS AND SYSTEMS

(75) Inventors: Erik Otto, San Francisco, CA (US);
David Horwitz, Los Altos, CA (US);
Kirk Harmon, San Ramon, CA (US);
Manoj Sharma, Milpitas, CA (US)

(73) Assignee: LifeScan, Inc., Milpitas, CA (US)

( * ) Notice: Subject to any disclaimer, the term of this patent is extended or adjusted under 35 U.S.C. 154(b) by 1106 days.

(21) Appl. No.: 11/395,024

(22) Filed: Mar. 31, 2006

(65) Prior Publication Data

US 2007/0232876 A1 Oct. 4, 2007

(51) Int. Cl.
*A61B 5/00* (2006.01)

(52) U.S. Cl. ....................................... 600/365

(58) Field of Classification Search ........... 600/365
See application file for complete search history.

(56) References Cited

U.S. PATENT DOCUMENTS

| | | | |
|---|---|---|---|
| 5,732,709 A | 3/1998 | Tacklind et al. | |
| 6,421,633 B1 | 7/2002 | Heinonen et al. | |
| 2003/0011646 A1* | 1/2003 | Levine et al. | 345/848 |
| 2003/0212317 A1* | 11/2003 | Kovatchev et al. | 600/365 |
| 2003/0216628 A1 | 11/2003 | Bortz et al. | |
| 2003/0229517 A1 | 12/2003 | Meserol et al. | |
| 2004/0096959 A1 | 5/2004 | Stiene et al. | |
| 2004/0153257 A1 | 8/2004 | Munk | |
| 2004/0225205 A1 | 11/2004 | Fine et al. | |
| 2007/0010950 A1* | 1/2007 | Abensour et al. | 702/19 |

FOREIGN PATENT DOCUMENTS

| | | |
|---|---|---|
| WO | WO 01/13786 | 3/2001 |
| WO | WO 01/72208 | 10/2001 |
| WO | WO 2004/015539 | 2/2004 |
| WO | WO 2004/023972 | 3/2004 |

OTHER PUBLICATIONS

E.A. Ryan, et al. "Assessment of the Severity of Hypoglycemia and Glycemic Lability in Type 1 Diabetic Subjects Undergoing Islet Transplantation" Diabetes, vol. 53, Apr. 1, 2004, 955-962 XP002558127.
European Search Report, EP Appln. No. 07251389.8, dated Nov. 30, 2009, The Hague, Netherlands, 5, pgs.

* cited by examiner

*Primary Examiner*—Patricia C Mallari

(57) ABSTRACT

The present invention relates to methods and systems for monitoring the effectiveness of diabetes treatment. Methods and systems in accordance with the present invention provide information relating to variability of glucose levels and hypoglycemia and hyperglycemia. Such information is based on time-stamped blood glucose data obtained from a meter or the like and actual measurements of HbA1c levels are not required.

7 Claims, 3 Drawing Sheets

DIABETES MANAGEMENT METHODS AND SYSTEMS

TECHNICAL FIELD

The present invention relates to diabetes management. More particularly, the present invention relates to methods and systems for monitoring the effectiveness of diabetes treatment.

BACKGROUND

The basic problem that diabetic patients have relates to the transfer of sugar, contained in the blood, across cell membranes. This in turn makes it difficult for the body to maintain sugar levels in the blood at the correct level. In the treatment of diabetes, patients regularly check blood glucose levels using a self-testing kit. By comparing the result of a self-test with the blood glucose level considered normal, a patient is able to estimate the amount of insulin that should be taken to keep the blood glucose level near normal. Too much blood sugar (e.g. due to the patient injecting too little insulin) or eating more than the prescribed amount is defined as hyperglycemic while too little blood sugar (e.g. due to the patient injecting too much insulin) is defined as hypoglycemic. These are considered to be short-term complications of diabetes and can cause acute symptoms or be a factor in the development of long-term complications. Diabetic patients can also suffer problems arising from their condition that only become apparent in the longer term. These problems are caused by excessive levels of sugar in the blood that result in, among other causes, sugar combining with protein to form glycosylated protein. Glycosylated protein is substantially insoluble and gives rise to thickening of the walls of veins and arteries, and thickening of the myelination of nerves.

One particular form of glycosylated protein is glycosylated hemoglobin. As glycosylated hemoglobin tends to remain in the blood, it provides an excellent indication of the level of glycosylated protein in the blood and therefore of the effectiveness of the treatment regime a patient has been following, as well as indicating how well the patient is following that regime.

Glycosylated hemoglobin includes three components; namely, HbA1a, HbA1b, and HbA1c. It has been shown that a normal level of HbA1c in a diabetic patient's blood is a good indication that the treatment regime is effective and the risk of secondary complications of diabetes is low. The level of HbA1c in a healthy person's blood is between 4% and 6% of the total hemoglobin while in a diabetic person the level may be significantly higher (e.g. greater than 8%). It is generally sought to reduce the level of HbA1c in a diabetic patient's blood to between 6% and 7%. The HbA1c level reflects the idiosyncratic (i.e. patient-specific) effectiveness of blood glucose treatment over a period of several months preceding the HbA1c measurement. The HbA1c level is commonly measured by laboratory tests in order to provide information related to the long term effectiveness of diabetes treatment.

While HbA1c protein levels provide valuable information, HbA1c levels are measured infrequently for typical patients and give no indication as to the variability associated with a patient's glycemic control or the propensity for hypoglycemia or hyperglycemia. For example, a patient may have an acceptable HbA1c level ranging between 4% and 7% but may have frequent hypoglycemic and/or hyperglycemic episodes because such episodes are not reflected in an HbA1c level.

Information relating to variability can be useful to a patient with diabetes or their clinician for a number of reasons. High variability can indicate brittle diabetes and may also indicate that a patient is not compensating for hypoglycemia and hyperglycemia adequately. A high variability may also indicate an increased risk of severe hypoglycemia, diabetic ketoacidosis and other acute complications, and therefore a patient with higher variability should be monitored more closely and this information should be taken into account when adjusting a therapeutic regimen.

SUMMARY

The present invention thus provides methods and systems that can provide information pertaining to variability of glucose levels and historical propensity for hypoglycemia and hyperglycemia. Information provided in accordance with the present invention is based on time-stamped blood glucose data obtained from a meter or the like and actual measurements of HbA1c levels are not required. That is, an estimated HbA1c level is determined and used in accordance with the present invention.

Accordingly, in an aspect of the present invention, a method of managing blood glucose data is provided. The method comprises the steps of providing a plurality of blood glucose data collected over a predetermined period of time, estimating an idiosyncratic HbA1c level from the plurality of blood glucose data using a first predetermined algorithm having at least one exclusion criteria, calculating an idiosyncratic variability index of glycemia from the plurality of blood glucose data using a second predetermined algorithm having at lest one exclusion criteria, and comparing the idiosyncratic variability index of glycemia and the idiosyncratic HbA1c level. Such exclusion criteria preferably include a history of testing, a frequency of tests per day, and a randomness of data on a daily basis.

In another aspect of the present invention, a user can access new variability information on a desired basis, weekly for example, on their personal blood glucose meter or blood glucose data management system. A blood glucose data management system in accordance with the present invention can include any personal device or software program used to house data such as a blood glucose monitor, PDA, cell phone, pocket book computer, insulin pump, insulin doser, Internet interface, or computer program. The information relating to the variability index and interfacing elements can also be housed within a data module or "smartchip" for upgrades to software on mobile devices or other software.

In another aspect of the present invention, a user can access a variability index from a health summary or status list of one or more analytical blood glucose tools. When selected the meter or blood glucose data management system can compute the variability index. Preferably, the value of the index will not be generated if the meter data meets certain exclusion criteria relating frequency of testing. If one has been generated for a given week, for example, the meter will preferably output that estimate. If no estimate has been generated previously for a given week, and the exclusion criteria has not allowed an estimate to be generated, the meter or blood glucose data management system will preferably output information relating to why an estimate could not be produced (i.e., which exclusion criteria were triggered by the data set).

In yet another aspect of the present invention, a user can access a variety of tools that analyze current and historical variability indexes for one or more of weekly trending, monthly graphical analysis, contextual information about variability, and recommended action and feedback. Regarding weekly trending, the data management system can preferably output trends in HbA1c levels on a weekly or other desired basis. This allows the user to track changes in glucose variability due to therapy changes over time and get timely feedback if it is slipping or improving. Displays of trending of variability levels may also be shown on a monthly basis depending on user preference. The data management system can also preferably output an overview of variability indexes on a monthly or other desired basis. This allows the patient and their doctor to determine seasonal or monthly variations in variability of glucose levels to determine when there might have been trouble spots during the year for the patient in terms of maintaining level control. The variability index can also be shown with contextual information about how idiosyncratic variability compares to the broader population, and to understand the associated risk for acute complications in the glucose variability index cohort that they belong to. The display may also output recommended action or feedback based on variability index or trends in variability indices. For example, the system may output a positive message to the patient when variability is improving on a weekly, monthly, or other basis.

DETAILED DESCRIPTION

Figure 1:
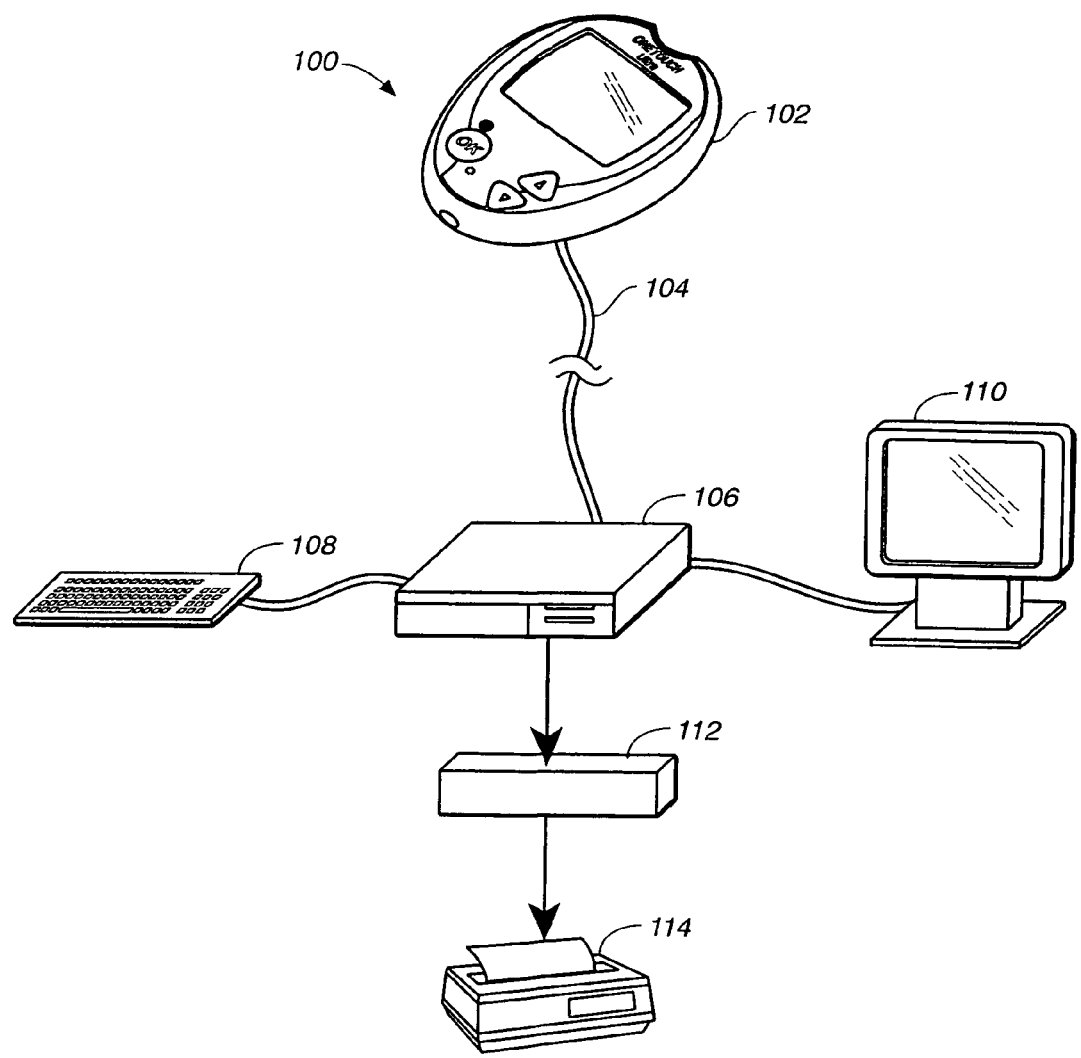
FIG. 1 is a schematic diagram of an exemplary system that can provide variability indices of glycemia and estimated HbA1c levels in accordance with the present invention.

FIG. 1 illustrates an exemplary system 100 that includes program 112 for computing variability indices of glycemia and estimated HbA1c levels in accordance with the present invention. System 100 preferably includes a data source 102, a communications link 104, a processing station 106 connected to one or more data input devices 108, a visual display 110, and an output device 114. Examples of data source 102 include, but are not limited to, a blood glucose metering system, a continuous metering system for detecting glucose in blood or interstitial fluid as described in U.S. patent application Ser. No. 10/432,827 (filed on Dec. 29, 2003), which is fully incorporated herein by reference for all purposes, and a metering system for detecting other analytes or indicators (e.g. cholesterol or HbA1c,) in any bodily fluid (e.g. blood, urine, interstitial fluid, etc). Data source 102 is preferably connected to processing station 106 via communications link 104. Examples of communications link 104 include, but are not limited to, a direct serial or USB cable, a TCP/IP or Ethernet based network connection and a wireless connection using protocols such as 802.11, InfraRed or Bluetooth. Processing station 106 preferably includes a module to save and store information used in the present invention (e.g., a database; not shown) and a module to process data (e.g., a central processing unit or CPU) from data sources 102 using algorithms. Examples of processing station 106 include, but are not limited to, a personal or networked computer, a personal digital assistant (PDA), a blood glucose metering system, or a mobile telephone. The term 'mobile telephone' as used herein refers to any portable device which utilizes wireless telephonic communication including conventional cellular telephones and combined cellular telephone/personal digital assistant (PDA) devices. Examples of input devices 108 include, but are not limited to, a keyboard, keypad, a mouse, a joystick, and a stylet. Examples of visual display 110 may include, but are not limited to, a display monitor for a personal or networked computer, a Liquid Crystal Display (LCD) for a personal digital assistant (PDA), mobile telephone, or a blood glucose metering system. Examples of output devices 114 include, but are not limited to, a printer, a fax machine, an email message, a text message, and a file that is stored on processing station 106.

Processing station 106 further preferably includes program 112 for computing variability indices of glycemia and estimated HbA1c levels in accordance with the present invention. A variability index can be calculated by a number of methods. Standard statistical methods can be used and include, but are not limited to, standard deviation, coefficient of variation, the percent out of a desired range, variance, range, and the interquartile range. These methods may also include more complex indices derived from glucose data that better represent clinically relevant fluctuations. These indices may also incorporate complex algorithms including, but not limited to, algorithms incorporating high and low blood glucose indices, rate of change of glucose and other factors. As an example, the standard deviation is used as the variability index. Accordingly, equation (1) is preferably used to calculate the standard deviation.

$$\text{Standard Deviation} = \sqrt{\frac{\sum (X - M)}{n - 1}} \quad (1)$$

Where:
$\Sigma$=sum of
X=individual glucose value
M=mean of glucose values; and
n=number of glucose values Estimated HbA1c levels can be calculated in a number of ways known to those skilled in the art. Examples of methods that can be used to estimate HbA1c include, but are not limited to, those described in International Application Nos. PCT/US01/09884 (published as WO 01/72208 on Oct. 4, 2001) and PCT/US2003/025053 (published as WO 2004/015539 on Feb. 19, 2004), both of which are fully incorporated herein by reference for all purposes.

An exemplary method of estimating HbA1c levels in accordance with the present invention preferably includes three steps: 1) pre-processing of data; 2) estimating HbA1c using at least one of four predetermined formulae, and 3) validation of the estimate via sample selection criteria. The data preferably comprises blood glucose data collected over a first predetermined period of time. The first predetermined period of time preferably ranges from about 45 days to about 90 days or more preferably, from about 45 days to about 60 days.

In the first step, pre-processing of the data for each patient preferably comprises: conversion of plasma to whole blood blood glucose (BG) (mg/dL); conversion of BG measured in mg/dL to units of mmol/l; and computing a Low Blood Glucose Index (RLO1) and a High Blood Glucose Index (RHI1). Preprocessing of the data for each patient preferably includes: conversion of plasma to whole blood BG mg/dL via BG=PLASBG (mg/dL)/1.12; conversion of BG measured in mg/dL to units of mmol/l via BGMM=BG/18; and computing RLO1 and RHI1. Preprocessing of the data further preferably uses a formula defined as Scale=$[\ln(BG)]^{1.0845} - 5.381$, wherein BG is measured in units of mg/dL; Risk1=22.765 (Scale)$^2$, wherein RiskLO=Risk1 if (BG is less than about 112.5) and therefore risk of LBGI exists, otherwise RiskLO=0; RiskHI=Risk1 if (BG) is greater than about 112.5) and therefore risk of HBGI exists, otherwise RiskHI=0; BGMM1=average BGMM per patient; RLO1=average of RiskLO per patient; RHI1=average of RiskHI per patient; L06=average of RiskLO computer only for readings during the night, otherwise missing if there are no readings at night; N06, N12, N24 are percentage of SMBG readings in time intervals; NC1=total number of SMBG readings in the first predetermined duration; and NDAYS=number of days with SMBG readings in the first predetermined duration. The N06, N12, N24 are percentage of SMBG readings in time intervals of about 0-6:59 hour time period, about 7-12:59 hour time period, and about 18-23:59 hour time period, respectively, or other desired percentages and number of intervals.

The method further preferably comprises assigning a group depending on the patient's computer High BG Index using predetermined criteria. Such criteria may be defined as: if (RHI1 is $\leq$about 5.25 or if RHI1 is $\geq$about 16) then the assigned group=0; if (RHI1 is >about 5.25 and if RHI1 is <about 7.0) then the assigned group=1; if (RHI1 is $\geq$about 7.0 and if RHI1 is <about 8.5) then the assigned group=2; and if (RHI1 is $\geq$about 8.5 and if RHI1 is <about 16) then the assigned group=3.

Next, the method may further include providing estimates using predetermined formula defined as: E0=0.55555*BGMM1+2.95; E1=0.50567*BGMM1+ 0.074*L06+2.69; E2=0.55555*BGMM1−0.074*L06+2.96; E3=0.44000*BGMM1+0.035*L06+3.65; and if (Group=1) then EST2=E1, or if (Group=2) then EST2=E2, of if (Group=3) then EST2=E3, otherwise EST2=E0.

Regarding step 2, the method preferably comprises providing further correction of the estimates using predetermined criteria defined as: if (missing(L06)) EST2=E0, if (RLO1 is $\leq$about 0.5 and RHI1 is $\leq$about 2.0) then EST2=E0−0.25; if (RLO1 is $\leq$about 2.5 and RHI1 is >about 26) then EST2=E0−1.5*RLO1; if ((RLO1/RHI1) is $\leq$about 0.25 and L06 is >about 1.3) then EST2=EST2−0.08.

The estimation of HbA1c of a patient based on BD data collected over the first predetermined duration can be accomplished by estimating HbA1c using at least one of four predetermined formulae defined as:

HbA1c=the EST2 defined above or as corrected above;

HbA1c=0.809098*BGMM1+0.064540*RLO1− 0.151673*RH1+1.873325, wherein BGMM1 is the average BG (mmol/l), RLO1 is the Low BG Index, RHI1 is the High BG Index;

HbA1c=0.682742*HBA0+0.054377*RHI1+1.553277, wherein HBA0 is a previous reference HBA1c reading taken about a second predetermined period or duration prior to the estimate, wherein RHI1 is the High BG Index; or HbA1c=0.41046*BGMM+4.0775 wherein BGMM1 is the average BG (mmol/l). The second predetermined duration preferably ranges from about 2.5 months to 6 months, and more preferably from about 2.5 months to about 3.5 months, or as desired.

Preferably, the validation of the estimate using the sample selection criteria of HbA1c estimate is achieved only if the first predetermined duration sample meets at least one of the following four criteria:

a test frequency criterion wherein if the first predetermined duration sample contains an average of at least about 1.5 tests to about 2.5 tests per day;

an alternative test frequency criterion only if the predetermined duration sample contains at least a third predetermined sample period or duration with readings with an average frequency of about 1.8 readings/day (or other desired average frequency);

a randomness of data criterion-1 wherein the HbA1c estimate is validated or displayed only if the ratio (RLO1/ RHI1 is $\geq$about 0.005), wherein: RLO1 is the Low BG Index, RHI1 is the High BG Index; and a randomness of data criterion wherein HbA1c estimate is validated or displayed only if the ratio (N06$\geq$about 3%), and wherein N06 is the percentage of readings during the night. The third predetermined duration is preferably at least 35 days and preferably ranges from about 35 days to about 40 days, or from about 35 days to about as long as the first predetermined duration, or as desired.

Program 112 preferably controls processing station 106 to perform one or more steps in accordance with the present invention. Program 112 preferably utilizes standard user interfaces (e.g. menus and dialogs) to permit a user to access its functions. Program 112 may be written in any computer language as a matter of design choice and may be stored on any computer-readable memory device such as a hard drive coupled with a computer processing unit.

Program 112 preferably includes an analysis portion and a reporting portion. Program 112 may provide access to algorithms for data sorting and analysis as well as expert system tools to help users control processes of program 112. Input data from data sources 102 are incorporated into program 112 then analysis unit analyzes input data to determine if specific exclusion criteria (see Table 1) are met. If exclusion criteria are not met, then reporting unit preferably generates a report for a patient or a professional user (e.g., a physician, a diabetes educator, or a nurse), as will be described below. If exclusion criteria are met, then computer program 112 preferably sends to visual display 110 of processing station 106 and/or the metering system a text message that indicates why a report was not generated. For example, a report would not be generated if too few blood glucose test results were recorded and stored within processing station 106 during a specific time period. A report is preferably generated when all desired exclusion criteria are not met and includes an estimated HbA1c level calculated as described previously. The estimated HbA1c level may range from about 4 percent to about 12 percent.

Table 1 comprises a list of exclusion criteria that a patient or professional user can define (left column) or that can be set by the manufacturer (right column).

TABLE 1

List of Exclusion Criteria

| Patient or Professional user-defined exclusion criteria | Manufacturer-defined exclusion criteria |
|---|---|
| HbA1c above 10% | Testing less than an average of two to four times per day, |
| HbA1c above 9% | Ratio of index low blood glucose values to index of high blood glucose values is very low |
| Type 2 diabetes on oral therapy | Readings not randomly spread throughout the day (i.e. high percentage of readings take place at one time of day on modal day graph |
| Type 2 diabetes | Very few readings at night |
| Gestational diabetes | Too many missing days of data in a row |
| Less than 20 years of age | Insufficient number of total days of data |
| Between 10 and 20 years of age | No prior HbA1c value to calibrate the estimation of HbA1c |

Figure 2:
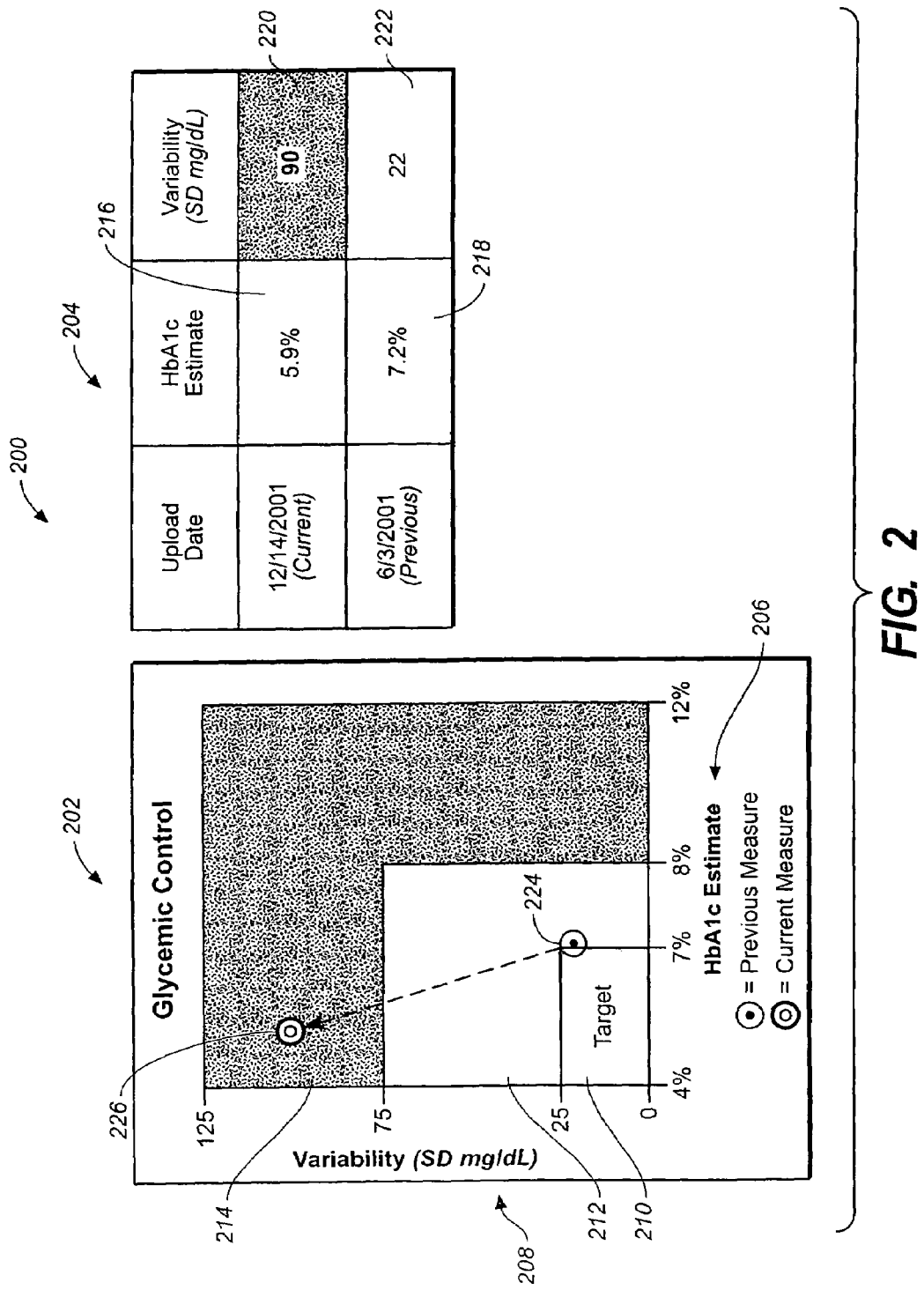
FIG. 2 is an illustrative output that can be generated and sent to a visual display and used for managing blood glucose in accordance with the present invention.

FIG. 2 is an exemplary output 200 generated for glycemic control that may be sent to a visual display 110 of processing station 106 and/or a metering system by program 112 in accordance with the present invention. Output 200, as shown, includes a graphical form 202 and, optionally, a tabular form 204. Graphical form 202 preferably reports the variability indices 208 as a function of the corresponding estimated HbA1c levels 206 as calculated by program 112.

Graphical form 202, as shown, includes three regions: a target zone 210, a cautionary zone 212, and a danger zone 214. Regions of graphical form 202 may be colored to provide ease of use for a patient or professional user. Target zone 210 is preferably defined as HbA1c levels ranging from about 4 percent to about 7 percent and variability ranging from about 0 mg/dL to about 25 mg/dL. Cautionary zone 212 is preferably defined as HbA1c levels ranging from about 7 percent to about 8 percent and variability ranging from about 25 mg/dL to about 75 mg/dL. Danger zone 214 is preferably defined as HbA1c levels ranging from about 8 percent to about 12 percent and variability ranging from about 75 mg/dL to about 125 mg/dL.

If a result is in danger zone 214, the patient should follow the advice of their physician to reduce the variability and the HbA1c level. If both the HbA1c level and variability are high, the patient may want to try to reduce variability first, because some of the intensive programs to reduce the HbA1c level incite more variability. To reduce variability the patient may attempt to identify more variable periods of the day and determine what their diabetes management behavior is at that time. For example if they are highly variable after exercising they may want to test more at that time or change the kind of exercise they are doing. Similarly, they may be highly variable because they are eating a meal for which they cannot quantify carbohydrates properly, in which case they should choose a food that is easier to quantify such that they can more easily calculate the amount of insulin to take.

Tabular form 204 preferably provides a numeric value for each of the current and previous estimated HbA1c levels 216, 218, respectively, and variability indices 220, 222 respectively. Tabular form 204 may be color coded similarly to regions of graphical form 202 to provide ease of use for a patient or professional user. Estimated HbA1c levels and variability indices are preferably calculated on a weekly and/or a monthly basis. A patient or professional user may set the specific day on which program 112 calculates the HbA1c levels and variability index. Referring to FIG. 2, for exemplary purposes only, graphical form includes a current data point 224 and a previous data point 226 that is listed in tabular form 204.

Figure 3:
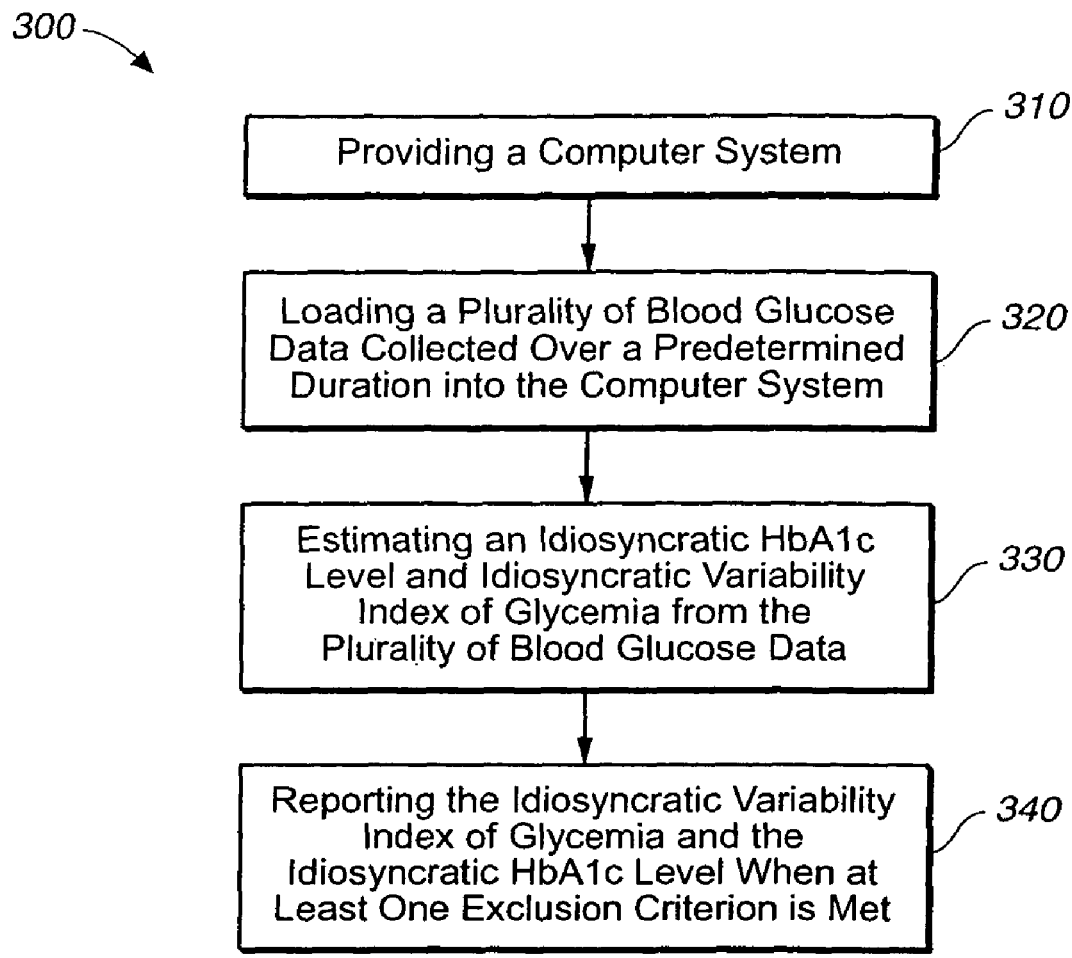
FIG. 3 is a flowchart illustrating an exemplary sequence of steps for managing blood glucose in accordance with the present invention.

FIG. 3 is a flowchart illustrating an exemplary sequence of steps of a method for using program 112 in accordance with the present invention. Method 300 includes first providing computer system 100 as described above with respect to FIGS. 1 and 2 and as set forth in step 310. The provided computer system 100 preferably includes a method for inputting, processing, and reporting information associated with diabetes management, as will be described below. During method 300, blood glucose test results are preferably integrated (e.g. uploaded or accessed) into program 112. Program 112 then analyzes the information using analysis portion and reports results using reporting portion, as will be described below.

Next, a plurality of blood glucose data collected over a predetermined period of time is loaded into the computer system 100 as set forth by step 320. Any blood glucose metering system that includes a date and time stamp record with each blood glucose test can be used as a data source 102 to collect the plurality of blood glucose data and transferred via a communications link 104 to a process station 106 that includes program 112. Program 112 can also be incorporated into any blood glucose metering system that is capable of recording a time and date with a blood glucose test result.

Program 112 then preferably analyzes the plurality of blood glucose data to estimate idiosyncratic HbA1c levels and to provide idiosyncratic variability index of glycemia as set forth by step 330. At periodic intervals, for example, weekly or monthly, as set by a patient or professional user, program 112 computes an estimate of an idiosyncratic HbA1c level based on inputted blood glucose data for the preceding period. Program 112 also preferably computes an idiosyncratic variability index as determined by a professional user.

Finally, program 112 preferably compares variability indices as a function of HbA1c levels and optionally generates a table as set forth by step 340 and as illustrated by FIG. 2. Program 112 preferably sends output 200 to visual display 110 of processing station 106 for a user to see. Output 200 may include a graphical form 202 and a tabular form 204. Graphical form 202 preferably includes three regions: a target zone 210, a cautionary zone 212, and a danger zone 214. Regions of graphical form 202 may be colored to provide ease of use for a patient or professional user. Target zone 210 is preferably defined as HbA1c levels ranging from about 4 percent to about 7 percent and variability ranging from about 0 mg/dL to about 25 mg/dL. Cautionary zone 212 is preferably defined as HbA1c levels ranging from about 7 percent to about 8 percent and variability ranging from about 25 mg/dL to about 75 mg/dL. Danger zone 214 is preferably defined as HbA1c levels ranging from about 8 percent to about 12 percent and variability ranging from about 75 mg/dL to about 125 mg/dL. Tabular form 204 preferably provides a numeric value for each of the current and previous estimated HbA1c levels 216, 218, respectively, and variability indices 220, 222 respectively. Tabular form 204 may be color coded similarly to regions of graphical form 202 to provide ease of use for a patient or professional user. Estimated HbA1c levels and variability indices are preferably calculated on a weekly and/or a monthly basis but any desired time period can be used.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A system for managing blood glucose data, the system comprising:
    a processor programmed to:
        receive a plurality of blood glucose data collected over a predetermined period of time;
        provide an estimation of an idiosyncratic HbA1c level from the plurality of blood glucose data;
        provide a calculation of an idiosyncratic variability index of glycemia from the plurality of blood glucose data; and
        determine whether at least one exclusion criteria has been met and report the idiosyncratic variability index of glycemia and the idiosyncratic HbA1c level when at least one exclusion criterion is not met and does not report the idiosyncratic variability index of glycemia and the idiosyncratic HbA1c level when the at least one exclusion criteria is met and further, wherein the at least one exclusion criterion includes a frequency of tests per day.

2. The system of claim 1, wherein the processor is programmed to report the idiosyncratic variability index of glycemia as a function of the idiosyncratic HbA1c level on a weekly basis.

3. The system of claim 1, wherein the processor is programmed to report the idiosyncratic variability index of glycemia as a function of the idiosyncratic HbA1c level on a monthly basis.

4. The system of claim 1, wherein the processor is programmed to report the idiosyncratic variability index of glycemia and the idiosyncratic HbA1c level in tabular form.

5. The system of claim 1, wherein the processor is programmed to estimate the idiosyncratic HbA1c level from a previously measured HbA1c level.

6. The system of claim 1, further comprising a blood glucose measurement device.

7. The system of claim 1, further comprising a memory device.

* * * * *